United States Patent [19]

Källstrand et al.

[11] Patent Number: 4,994,260

[45] Date of Patent: Feb. 19, 1991

[54] PHARMACEUTICAL MIXTURE

[75] Inventors: Anders G. V. Källstrand, Dalby; Kjell J. Mattson, Södertälje; Rolf I. Sjöqvist, Gnesta, all of Sweden

[73] Assignee: Astra Lakemedel Aktiebolag, Sodertalje, Sweden

[21] Appl. No.: 815,125

[22] Filed: Dec. 30, 1985

Related U.S. Application Data

[63] Continuation of Ser. No. 500,618, Jun. 3, 1983, abandoned, and a continuation-in-part of Ser. No. 668,168, Nov. 11, 1984, Pat. No. 4,656,027, which is a continuation-in-part of Ser. No. 383,148, May 25, 1982, abandoned.

[30] Foreign Application Priority Data

Jun. 24, 1982 [SE] Sweden ................ 8203953

[51] Int. Cl.$^5$ .................. A61K 9/36; A61K 9/62
[52] U.S. Cl. .................. 424/10
[58] Field of Search .................. 424/10,35

[56] References Cited

U.S. PATENT DOCUMENTS

| | | | |
|---|---|---|---|
| 3,109,775 | 11/1963 | Shepard et al. | 424/20 |
| 3,549,746 | 12/1970 | Gravateh et al. | 424/35 |
| 3,626,056 | 12/1971 | Granatek et al. | 424/35 |
| 3,821,422 | 6/1974 | Morse et al. | 424/35 |
| 3,860,733 | 1/1975 | Morse et al. | 424/35 |
| 4,016,254 | 5/1977 | Seager | 424/35 |
| 4,321,253 | 3/1982 | Beatty | 424/35 |
| 4,656,027 | 4/1987 | Sjöövist | 424/35 |

FOREIGN PATENT DOCUMENTS

| | | |
|---|---|---|
| 0040590 | 11/1981 | European Pat. Off. . |
| 0068324 | 1/1983 | European Pat. Off. . |
| 2432941 | 7/1975 | Fed. Rep. of Germany . |
| 1293329 | 10/1972 | United Kingdom . |
| 1506016 | 4/1978 | United Kingdom . |

OTHER PUBLICATIONS

Remington Pharm Science, 15th Edition, p. 1235.
"Solubility of the Xanthines, Antipyrine, and Several Derivatives in Syrup Vehicles", Anthony N. Paruta and Bhogilal B. Sheti, J. Pharmaceutical Sciences, vol. 55, No. 9, Sep. 1966, pp. 896–901.

*Primary Examiner*—Stanley J. Friedman
*Attorney, Agent, or Firm*—White & Case

[57] ABSTRACT

A pharmaceutical mixture with controlled release of actice substance which includes masking of bad taste and stability increasing of active substance characterized in that an encapsulated active substance is combined with a substance controlling the release of active substance from the encapsulation and method for preparing said mixture.

7 Claims, No Drawings

PHARMACEUTICAL MIXTURE

This application is a continuation of Ser. No. 500,618, filed on June 3, 1983 and now abandoned and also this application is a continuation-in-part of copending U.S. patent application Ser. No. 668,168, filed Mar. 11, 1984, now issued as U.S. Pat. No. 4,656,027, which is a continuation-in-part of U.S. patent application Ser. No. 383,148 filed May 28, 1982 and now abandoned.

DESCRIPTION

1. Technical Field

The present invention is concerned with an oral pharmaceutical preparation containing an encapsulated pharmaceutically active substance. More specifically the preparation is a dry powder for mixture or said dry powder dissolved in an aqueous solution.

The object of the invention is to provide a preparation wherein the dissolution of the active substance from the encapsulation is controlled.

2. Background Art

Among alternative forms of orally administering pharmaceutically active substances the use of a solution or a suspension of the active principle in an aqueous solution is a form often seen in pediatric use. This preparation is called a mixture. The dry powder including the active principle and adjuvants which is to be dissolved or suspended is called dry powder for mixture.

The preparation is stored as a dry powder. Before administration the dry powder is dissolved or suspended in an aqueous solution giving rise to a liquid formulation for oral administration—a mixture. Alternatively the mixture can be prepared in the factory and stored at least for two years prior to administration. Pharmaceutically active substances for use in mixtures have been encapsulated either to mask bad taste or to control the release in the body.

Hitherto medicines have been coated with polymers or with polymers in combination with plasticizers to control drug release (microencapsulation). Applied on granulates of a drug it retards the rate of dissolution.

The main way to control drug dissolution from microcapsules is the amount of polymer applied, in order to obtain the expected plasma profile of the drug. This can also be obtained by adding water soluble substances to the coat during the coating process.

DISCLOSURE OF THE INVENTION

The present invention provides a mixture, wherein bad taste of the drug is masked and/or it provides a mixture with retarded dissolution to obtain slow release effect.

The mixture is obtained either by suspending the dry powder in an aqueous solution or by suspending the microcapsules in a solution of the release controlling substance.

The drug release from the microcapsules within the mixture, here called leakage, is very low, but in the body the drug is released from the microcapsules and available for absorption.

This invention also provides for increased drug stability in the mixture.

This result is obtained by adding to the encapsulated active substance and customary adjuvants a release-controlling substance (sink).

As sink can be used a carbohydrate or a carbohydrate-related compound, for instance a poly- or a oligosaccharide such as dextrane; a disaccharide such as saccharose, maltose or lactose, a monosaccharide such as glucose, fructose, galactose, mannose or xylitol; a carbohydrate-related compound such as mannitol, sorbitol, glycerol, glycol, a glycoside of a monosaccharide or a substance derived from ethyleneglycol for instance polyethyleneglycol (trade names Carbowaxes: and Carbopoles ®).

As sink can one or a mixture of two or more of the mentioned substances be used.

The amount of sink should be between 40% and 99% (weight/weight), preferably 60-75% (weight/weight) of the entire preparation, that is of the ready to use suspension for oral administration (the mixture).

An alternative to adding the release-controlling substance to the encapsulated drug is to encapsulate the release-controlling substance together with the drug within the encapsulating shell.

Sugars that can be used according to the invention are among others sucrose, glucose, fructose and sorbitol.

As pharmaceutically active substance any drug can be used, for instance anyone of the following:

| | |
|---|---|
| Chemotherapeutics | bacampicillin, ampicillin, flucloxacillin, tetracycline, dicloxacillin, chloramphenicol, gentamicin, erythromycin, lincomycin, rifampicin, sulphadiazine, sulphamethoxypyridazine, griseofulvine, nitrofurantoine |
| Adrenergis and beta-receptor-stimulators | ephedrine, terbutaline, theophylline, enprophylline |
| Expectorants and cough depressants | Ethylmorphine, dextromethorphan, noscapine, bromhexine |
| Heartglucosides and antiarythmics | Digitoxine, digoxin, dispyramide, procainide, tocainide, alprenolol, atenolol, metoprolol, pindolol, propranolol |
| Blood pressure depressants | betanidine, clonidine, guanetidine, methyldopa, reserpine trimetaphane, hydrolazine, bendrophlumetiazide, furosemide, chlorotiazide |
| Antihistamines | brompheniramine, chlorcyclizine, chlorpheniramine, diphenhydramine, prometazine |
| Peroral antidiabetes | carbutamide, chlorpropamide, tolazamide, tolbutamide |
| Sedatives Hypnotics Antidepressants | hexobarbital, pentobarbital, phenobarbital, meprobamate, chlordiazepoxide, diazepam, flunitrazepam, nitrazepam, oxazepam, chlormethiazol, chlor- |

| | -continued |
|---|---|
| | promazine, fluphenazine, perphenazine, prochlor-perazin, haloperidol, lithium, alaproclate, zimeldine, amitryptiline, imipramine, nortriptyline |
| Antiepileptics | phenytoine, ethotoin, ethosuximide, carbamazepine |
| Analgetics | codeine, morphine, pentazocine, petidine, dextro- |
| Anesthetics | propoxyphene, methadone, acetylsalicylic acid, diflunisal, phenazone, phenylbutazon, acetamino-phene, indometazine, naproxen, piroxicam, lidocaine, etidocaine |
| Others | cimetidine, quinidine, dicoumarine, warfarine, potassium chloride, chloroquine |

The preferred drug is bacampicillin hydrochloride (1'-ethoxycarbonyloxyethyl 6-[D(−)-2-amino-2-phenylacetamido]-penicillanate hydrochloride), other epimeric forms and the racemic form of bacampicillin hydrochloride.

Other preferred drugs are theophylline, enprophylline and erythromycine.

The drugs mentioned above are used in neutral or salt form.

The following salts of the drugs mentioned above can be used:

Acetate, benzenesulfonate, benzoate, bicarbonate, bitartrate, bromide, calcium edetate, camsylate, carbonate, chloride, citrate, dihydochloride, edetate, edisylate, estolate, esylate, fumarate, gluceptate, gluconate, glutamate, clycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulphate, tannate, tartrate, teoclate, triethiodide.

Also the further cationic salts can be used. Suitable cationic salts include the alkali metal, e.g. sodium and potassium, and ammonium salts and salts of amines known in the art to be pharmaceutically acceptable, e.g. glycine, ethylene diamine, choline, diethanolamine, triethanolamine, octadecylamine, diethylamine, triethylamine, 1-amino-2-propanol-2-amino-2-(hydroxymethyl)propane-1,3-diol and 1-(3,4-dihydroxyphenyl)-2-isopropylaminoethanol.

The encapsulation of the drug can be achieved in the form of microcapsules, but the encapsulation is not restricted to the micro size.

COATING MATERIAL

Polymers:

Synthetic polymers of polyvinyl type, e.g. polyvinylchloride, polyvinylacetate, polyvinylalcohol Polyethylene type, e.g. polyethylene, polystyrene Polymers of acrylic acid or acrylic acid ester type, e.g. methylmetacrylate or copolymers of acrylic monomers Biopolymers or modified biopolymers of cellulose, e.g. ethylcellulose, cellulose acetate phtalate.

The polymer can be water insoluble, acid soluble or alkaline soluble and mixed with plastisizer or other filler and water soluble modified biopolymer, e.g. hydroxy propyl cellulose.

Also fats and oils, wax, higher fatty acids, higher alcohols or polyhydric alcohols can be used as such or in combination.

In one embodiment of the invention bacampicillin hydrochloride (BAPC) is encapsulated in an insoluble, microporous polymer, such as ethyl cellulose and sucrose is used as sink to make a dry powder for mixture, which is then dissolved in water to make a mixture.

In another embodiment of the invention BAPC is encapsulated in a polymer soluble in acid, such as Eudragit ® E 100 and sucrose is used as sink to make a dry powder for mixture, which is then dissolved in water to make a mixture.

In a further embodiment of the invention theophylline is microencapsulated in a shell of ethyl cellulose and sorbitol is used as sink to make a dry powder for mixture, which is then dissolved in water to make a mixture.

In a further embodiment of the invention acetylsalicylic acid is encapsulated in a shell of cellulose acetate phtalate and sucrose is used as sink to make a dry powder for mixture, which is then dissolved in water to make a mixture.

A release controlling substance is mixed with other constituents and microcapsules of the drug are added to this dry powder and mixed in a conventional blender. This dry powder is then added to bottles in a filling machine. Water is then added, by the customer or at the pharmacy, to dissolve the release controlling substance.

Alternatively, a solution of the release controlling substance and other constituents is prepared. The microcapsules of the drug can then be added either to this solution and then filled into bottles ready to use, or the microcapsules of the drug can be filled into a separate container and be added by the customer or the pharmacy to the solution prior to use.

BEST MODE OF CARRYING OUT THE INVENTION

Leakage Studies

Leakage studies were carried out in order to show that the microcapsules will not release any significant amount of the drug into the sink causing bad taste in contact with water, causing degradation or losing its ability to work as controlled release formulation.

Microcapsules were added to sink solution according to the invention. The amount of drug which had been released from the microcapsules was analyzed. This is called leakage. The samples were in some instance stored up to 80 days in room temperature. The sink was analyzed spectrophotometrically. The result is given in percent leakage which is the amount of the drug which is in solution divided by the initial amount of microencapsulated drug.

In order to demonstrate the effect of the release controlling substance the release studies were also performed in water. Microcapsules were placed in a beaker and water was added. The stirring rate was 30 rpm and the amount of release was calculated as described above.

EXAMPLE 1

100 g of dry powder contains

| | |
|---|---|
| Bacampicillin hydrochloride ethyl cellulose microcapsules (70% drug) | 5.61 g |
| Sodium bicarbonate | 0.83 g |
| Mannitol | 9.35 g |
| Sucrose | 83.1 g |

Sodium bicarbonate, mannitol and sucrose were premixed before the microcapsules were added. The final mixing was carried out in a beaker. The mixture contains 46% w/w of release controlling substances.

4.81 g of the powder was added to 5 ml of water.

| Time (days) | Leakage (%) |
|---|---|
| 1 | 0.5 |
| 2 | 0.9 |
| 4 | 1.1 |
| 7 | 1.3 |
| 10 | 1.2 |

In this example the leakage of drug was analyzed with a mercurimetric titration method.

| Time (days) | Release in water (%) |
|---|---|
| 0.042 | 60 |
| 0.084 | 90 |

EXAMPLE 2

25.8 g of pharmaceutical mixture contains

| | |
|---|---|
| Bacampicillin hydrochloride Eudragit ® E 100 microcapsules (64% drug) | 0.80 g |
| Fructose | 18.75 g |
| Water | 6.25 g |

Fructose was dissolved in water before the microcapsules were added.

The mixture contains 67.5% release controlling substances.

| Time (hours) | Leakage (%) |
|---|---|
| 2 | 0.2 |

| Time (hours) | Release in water (%) |
|---|---|
| 0.008 | 50 |
| 0.05 | 90 |

EXAMPLE 3

31.3 g of pharmaceutical mixture contains:

| | | |
|---|---|---|
| Theophylline ethyl cellulose microcapsules (72% drug) | | 0.05 g |
| a | Fructose | 23.44 g |
| | Water | 7.82 g |
| b | Sorbitol | 20.94 g |
| | Water | 7.82 g |

The two mixtures were prepared according to Example 2.

The mixtures contain (a) 75% (b) 72% release controlling substance.

| Time (days) | Leakage (%) | |
|---|---|---|
| | (a) | (b) |
| 1 | <0.2 | 0.7 |
| 3 | <0.2 | — |
| 5 | <0.2 | — |
| 7 | <0.2 | — |
| 10 | <0.2 | — |

| Time (days) | Release in water (%) |
|---|---|
| 0.21 | 50 |
| 0.33 | 90 |

EXAMPLE 4

31.3 g of pharmaceutical mixture contains:

| | | |
|---|---|---|
| Theophylline ethyl cellulose microcapsules (72% drug) | | 0.05 g |
| a | Sucrose | 9.38 g |
| | Sorbitol | 9.38 g |
| b | Sucrose | 9.38 g |
| | Glycerol | 9.38 g |
| c | Glucose | 9.38 g |
| | Fructose | 9.38 g |
| | Water | 12.5 g |

The three mixtures were prepared according to example 2.

The mixtures contain 60% of release controlling substances.

| Time (days) | Leakage (%) | | |
|---|---|---|---|
| | (a) | (b) | (c) |
| 1 | 0.20 | <0.2 | 0.26 |
| 2 | 0.31 | 0.35 | 0.28 |
| 5 | 0.65 | 0.82 | 0.49 |
| 9 | 1.15 | 1.77 | 0.90 |

| Time (days) | Release in water (%) |
|---|---|
| 0.21 | 50 |
| 0.33 | 90 |

EXAMPLE 5

75.1 g of pharmaceutical mixture contains:

| | |
|---|---|
| Acetylic salicylic acid cellulose acetate phtalate microcapsules (69% drug) | 0.100 g |
| Sucrose | 48.75 g |
| Phosphate buffer (pH 7.0) | 26.25 g |

Sucrose was dissolved in the phosphate buffer. The microcapsules were then added.

The mixture contains 65% release controlling substance.

| Time (days) | Leakage (%) |
|---|---|
| 1 | 3.5 |

| Time (days) | Release in phosphate buffer pH 7.0 (%) |
|---|---|
| 0.008 | 50 |
| 0.017 | 90 |

EXAMPLE 6

|  | a | b | c |
|---|---|---|---|
| Bacampicillin hydrochloride ethyl cellulose microcapsules (70% drug) | 0.27 g | 0.27 g | 0.27 g |
| Sodium bicarbonate | 0.40 g | 0.40 g | — |
| Mannitol | 0.45 g | — | — |
| Sucrose | 4.0 g | — | — |
| Water | 5.0 g | 5.0 g | 5.0 g |

The mixtures were prepared according to Example 1.

The mixture (a) contains 44% of release controlling substance.

The release in water of the microcapsules were the same as in Example 1.

| Time (days) | Leakage (%) | | |
|---|---|---|---|
|  | a | b | c |
| 1 | 0.5 | 85 | 100 |
| 2 | 0.9 | | |
| 4 | 1.1 | | |
| 7 | 1.3 | | |
| 10 | 1.2 | | |

EXAMPLE 7

Four different microcapsules coated with ethylcellulose were suspended in sorbitol dissolved in water according to following composition.

| Microcapsules | 50 mg |
|---|---|
| Sorbitol | 45.1 g |
| Water | 19.3 g |

The mixtures contain 70% release controlling substance.

| Microcapsules | | Leakage in sorbitol sink | | Release in water | |
|---|---|---|---|---|---|
|  |  | (%) | (days) | (%) | (h) |
| KCl | (86)* | 16 | 21 | 56 | 3 |
| Paracetaminophene | (91)* | 19 | 21 | 35 | 1 |
| Flucloxacillin | (89)* | 20 | 1 | 90 | 0.5 |
| Fenoxymethyl penicillin potassium | (83)* | 10 | 1 | 80 | 1 |

*content of active drug in the microcapsule

EXAMPLE 8

0.2 g theophyllin microcapsules according to Example 3 were suspended in different sugar solutions

| Release controlling substance % (w/w) | Leakage (%) | Time (days) |
|---|---|---|
| Xylitol | 55 | 13 | 80 |
| Glucose | 50 | 17 | 40 |
| Sorbitol | 70 | 3 | 80 |
| Fructose | 75 | 3 | 80 |
| Fructose-xylitol | 19-41 | 10 | 80 |
| Fructose-xylitol | 38-28 | 6 | 80 |
| Fructose-xylitol | 56-14 | 4 | 80 |

It is thus possible to restrict the leakage in the mixture to only a few percent after almost three months storage in room temperature.

EXAMPLE 9

65.4 g of pharmaceutical mixture contains:

| Theophyllin wax coated microcapsules (52% drug) | 1 g |
|---|---|
| Sorbitol | 45.1 g |
| Water | 19.3 g |

The mixture was prepared according to Example 3.

The mixture contains 69% release controlling substance.

| Time (days) | Leakage (%) |
|---|---|
| 22 | 0.7 |

| Time (days) | Release in water (%) |
|---|---|
| 0.5 | 19 |

EXAMPLE 10

26.31 g of pharmaceutical mixture contains

| Prochloroperazin wax coated microcapsules (3.4% drug) | 10 mg |
|---|---|
| Sorbitol | 18 g |
| Water | 8.3 |

The mixture was prepared according to Example 3.

The mixture contains 70% release controlling substance.

| Time (days) | Leakage (%) |
|---|---|
| 12 | 2.7 |

| Time (days) | Release in water (%) |
|---|---|
| 0.25 | 28 |

EXAMPLE 11

27.15 g of pharmaceutical mixture contains:

| Theophylline ethyl cellulose coated microcapsules (72%) | 0.15 g |
|---|---|
| Polyethyleneglycol (Carbowax ® 400) | 20.25 g |
| Water | 6.75 g |

Polyethyleneglycol was mixed with water and the microcapsules were added.

The mixture contains 75% release controlling substance.

| Time (days) | Leakage (%) |
|---|---|
| 15 | 2.4 |

The release in water, see Example 3.

EXAMPLE 12

13.877 g of pharmaceutical mixture contains:

| | |
|---|---|
| Erythromycin cellulose acetate phtalate coated microcapsules (57% drug) | 0.877 mg |
| Fructose | 9.75 |
| Water | 3.25 |

The microcapsules were added to a solution of fructose in water.

The mixture contains 71% release controlling substance.

| Time (days) | Leakage (%) |
|---|---|
| 10 | <1 |

| Time (days) | Release in water (%) |
|---|---|
| 0.25 | 46 |

RELEASE STUDIES

Microcapsules were suspended in 75% release controlling substance solution and after two or three days storage the microcapsules were filtered off and the release of the drug was measured. The microcapsules were placed in a beaker containing either simulated gastric fluid or simulated intestinal fluid at 37° C in order to simulate the in vivo situation. The stirring rate was 30 rpm. Samples were withdrawn after certain time points and those were analyzed for drug content spectrophotometrically.

The results show time to obtain 50, 70 and 90 percent release of the total amount of microencapsulated drug.

| | Theophylline microcapsules | | | |
|---|---|---|---|---|
| Release | Simulated gastric fluid (hours) | | Simulated intestinal fluid (hours) | |
| (%) | Original | Stored 3 days | Original | Stored 2 days |
| 50 | 4.2 | 4.4 | 3.7 | 4.4 |
| 70 | 5.7 | 5.8 | 5.5 | 6.6 |
| 90 | 6.2 | 6.4 | 7.5 | 8.3 |

| | Acetylic salicylic acid | | | |
|---|---|---|---|---|
| Release | Simulated gastric fluid (%) | | Simulated intestinal fluid (hours) | |
| (%) | Original | Stored 2 days | Original | Stored 2 days |
| 50 | | | 0.14 | 0.21 |
| 70 | | | 0.22 | 0.31 |
| 90 | | | 0.3 | 0.5 |
| 1 h | 12% | 8% | | |
| 2 h | 25% | 15% | | |

| | Bacampicillin hydrochloride Eudragit ® E 100 microcapsules | | | |
|---|---|---|---|---|
| Release | Simulated gastric fluid (min) | | Simulated intestinal fluid (min) | |
| (%) | Original | Stored 2 days | Original | Stored 2 days |
| 50 | 0.4 | 0.8 | 1.5 | 3 |
| 70 | 0.5 | 0.9 | 1.8 | 3.7 |
| 90 | 0.7 | 1.0 | 2.5 | 5 |

| Microcapsule compositions as in Examples 7, 9 and 11. | | | | | |
|---|---|---|---|---|---|
| | Release in water | | | | |
| | Initially | | Storage time | | |
| Microcapsules | (%) | (h) | (days) | (%) | (h) |
| KCl | 56 | 3 | 14 | 53 | 3 |
| Paracetaminophene | 35 | 1 | 14 | 48 | 1 |
| Fenoxymethyl penicillin potassium (a) | 80 | 1 | 3 | 81 | 1 |
| Theophyllin wax coated (b) | 19 | 12 | 25 | 17 | 12 |
| Theophyllin ethyl cellulose coated (c) | 46 | 6 | 6 | 50 | 6 |

(a) according to Example 7
(b) according to Example 9
(c) according to Example 11

Release studies have also been carried out on the compositions in Example 8. The release rate was performed according to USP XX (method II paddle) 100 rpm in 900 ml 37° water.

The release rate is expressed as percent released per hour. The initial release rate was 12%/h.

| Release controlling substance | Release rate (%/h) | Time (days) |
|---|---|---|
| Xylitol | 9.9 | 80 |
| Glucose | 9.7 | 40 |
| Sorbitol | 11.7 | 80 |
| Fructose | 11.8 | 80 |
| Fructose-xylitol (19-41) | 10.5 | 80 |
| Fructose-xylitol (38-28) | 11.9 | 80 |
| Fructose-xylitol (56-14) | 11.9 | 80 |

The influence on storage time of the microcapsules in the different sink solution is negligible.

STABILITY STUDIES

Microcapsule suspensions were prepared with sink solutions according to the invention. The suspensions were stored and the drug content was measured with HPLC analysis as an selective and precise method.

Mixtures

Mixtures not according to the invention
- (a) According to Example 6 b
- (b) According to Example 6 c

- (c) According to Example 6 a
- (d) Bacampicillin HCl microcaps. (72% drug) ethylcellulose coated 0.36
  - Sucrose 8.32
  - Water 4.48
- (e) Bacampicillin HCl microcaps. (72% drug) ethyl cellulose coated 0.36
  - Fructose 9.6
  - Water 3.2 cont.
- (f) Acetyl salicylic acid microcaps. (69% drug) cellulose acetate phtalate coated 0.72
  - Sucrose 8.32
  - Citrate buffer pH 3 4.48
- (g) Erythromycin microcaps. 0.44 g -continued

| | (87% drug) cellulose acetate phtalate coated | |
|---|---|---|
| | Sucrose | 8.32 g |
| | Phosphate buffer pH 7.0 | 4.48 g |

| Mixture | Storage condition | | Intact drug* (%) |
|---|---|---|---|
| | time (days) | temp (°C) | |
| a | 1 | 25 | 2 |
| b | 1 | 25 | 60 |
| c | 10 | 25 | 91 |
| d | 7 | 25 | 83 |
| e | 7 | 25 | 89 |
| f | 30 | 50 | 70 |
| g | 30 | 50 | 82 |

*initially the amount of intact drug was 100

The results imply that mixtures according to the invention has an improving effect on the stability of drugs.

We claim:

1. A ready-to-use pharmaceutical preparation for controlled release of a pharmaceutically active substance which masks bad taste and increases stability of the pharmaceutically active substance prepared by mixing in an aqueous carrier a pharmaceutically active substance encapsulated in a coating and 60 to 99% by weight of a release controlling substance selected from the group consisting of polysaccharides, oligosaccharides, disaccharides, monosaccharides, polyhydroxy alcohols and mixtures thereof.

2. A pharmaceutical preparation according to claim 1, wherein in the release controlling substance is sucrose, glucose, fructose or sorbitol.

3. A pharmaceutical preparation according to claim 1, wherein in that the active substance is bacampicillin or theophylline.

4. A pharmaceutical preparation of claim 1, comprising 60 to 75% (weight/weight of the ready-to use mixture) of the release controlling substance.

5. A pharmaceutical preparation according to claim 1, wherein the aqueous carrier is water.

6. A ready-to-use pharmaceutical preparation according to claim 1, wherein the coating comprises a material selected from the group consisting of synthetic polymers of the polyvinyl type, polymers of the polyethylene type, polymers of acrylic acid or acrylic acid esters, cellulose, modified cellulose, fats, oils, waxes, fatty acids, higher alcohols, and polyhydric alcohols.

7. A ready-to-use pharmaceutical liquid preparation according to claim 1, wherein the coating comprises cellulose or a cellulose derivative.

* * * * *